United States Patent [19]

Davis

[11] Patent Number: 5,038,518

[45] Date of Patent: Aug. 13, 1991

[54] PROCESS FOR THE ECONOMICAL PRODUCTION OF SEEDS CAPABLE OF GROWING $F_1$ HYBRID COTTON

[76] Inventor: William H. Davis, 1109 Yonkers St., Plainview, Tex. 79072

[21] Appl. No.: 340,458

[22] Filed: Apr. 19, 1989

[51] Int. Cl.$^5$ .......................... A01H 1/00; A01H 1/02
[52] U.S. Cl. .......................................... 47/58; 800/200; 800/DIG. 63; 47/DIG. 1
[58] Field of Search ............................. 47/58, DIG. 1

[56] References Cited

U.S. PATENT DOCUMENTS

| | | | |
|---|---|---|---|
| 3,842,538 | 10/1974 | Barabus | 47/58 |
| 3,903,645 | 9/1975 | Bradner | 47/58 |
| 4,570,380 | 2/1986 | Ray et al. | |

FOREIGN PATENT DOCUMENTS 668452  8/1963  Canada .

OTHER PUBLICATIONS

Vaissiere et al. (1984), Agron. J., vol. 76, pp. 1005-1010.
Berger et al. (1988) Southwest Entamol. vol. 13, (1) pp. 47-54 (Abstract Relied on).
Pondy (1980), Heredity, vol. 45(1), pp. 15-30 (Abstract Relied On).
Poehlman (1987), *Breeding Field Corp.*, AVI Pub. Co. p. 560.
Vesta G. Meyer, "Male Sterility from *Gossypium harknessii*", J. of Heredity, vol. 66, pp. 23 to 27 (1975).
Joseph O. Moffett, Lee S. Stith and Charles W. Shipman, "Producing Hybrid Cotton Seed on the High Plains of Texas", Beltwide Cotton Production Research Conference Proceedings, Atlanta, GA, pp. 90 to 92, (1977).
J. B. Weaver, Jr., "Present Status of Fertility Restoration in Cytoplasmic Male-Sterile Upland Cotton", Beltwide Cotton Production Research Conference Proceedings, Atlanta, GA, pp. 95 to 96 (1977).
Joseph O. Moffett, Lee S. Stith and Charles W. Shipman, "Producing Hybrid Cotton Seed on a Field Scale by Using Honey Bees as Pollinators", Beltwide Cotton Production Research Conference Proceedings, Dallas, TX, pp. 77 to 79 (1978).
W. R. Meredith, Jr.; Vesta Meyer, B. W. Hanny and J. C. Bailey, "Influence of Five Gossypium Species Cytoplasms on Yield, Yield Components, Fiber Properties, and Insect Resistance in Upland Cotton", Crop Science, vol. 19, pp. 647 to 650, Sep.-Oct., 1979.
Richard H. Sheetz and James B. Weaver, Jr., "Pima Fertility Enhancer Factor: Inheritance and Use in Hybrid Cotton Production", Beltwide Cotton Production Research Conference Proceedings, St. Louis, MO, p. 82 (1980).
R. H. Sheetz and J. B. Weaver, Jr., "Inheritance of a Fertility Enhancer Factor from Pima Cotton When Transferred into Upland Cotton with *Gossympium harknessii* Brandegee Cytoplasm", Crop Science, vol. 20, pp. 272 to 275, Mar.-Apr., 1980.
Joseph O. Moffett, Henry B. Cobb and Don R. Rummel, "Bees of Potential Value as Pollinators in the Production of Hybrid Cottonseed on the High Plains of Texas", Beltwide Cotton Production Research Conferences Proceedings, Bee Report, No. 2, pp. 1 to 12 (1980).
Delbert C. Hess, "Hybrid Cotton Development", Beltwide Cotton Mechanization-Production Research Conferences Proceedings, New Orleans, LA, pp. 28 to 29 (1981).
J. E. Quisenberry and R. E. Dilbeck, "Stormproof Boll in Upland Cotton III. Genotype-Environment Interaction and Genetic Analysis", Crop Science, vol. 21, pp. 511 to 514, Jul.-Aug., 1981.
James B. Weaver, Jr., "Recent Significant Observations on the Development of Hybrid Cotton", Beltwide Cotton Production Research Conference Proceedings, Las Vegas, NV, pp. 88 to 90 (1982).

(List continued on next page.)

*Primary Examiner*—Elizabeth C. Weimar
*Assistant Examiner*—Gary Benzion
*Attorney, Agent, or Firm*—Burns, Doane, Swecker & Mathis

[57] ABSTRACT

An improved overall process is provided which makes possible the reliable production of seeds capable of growing $F_1$ hybrid cotton plants on an economically advantageous basis. A cotton planting area is selected which is suitable for habitation by ground-dwelling wild bees. The population of ground-dwelling wild bees is encouraged through the non-use of an insecticide of at least one growing season. During an immediately following growing season a portion of the planting area is planted with a block of early-blossoming plants which provide a source of pollen and nectar for the ground-dwelling wild bees during the spring and early summer. Another nearby section of the planting area during the immediately following growing season is planted with a substantially random population of cytoplasmically male sterile cotton plants and male fertile cotton plants which are capable of restoring male fertility to the progeny of the cytoplasmically male sterile plants. No insecticide is applied to the cotton plants at least until after seed set has occurred. Pollination of the cotton plants is accomplished during mid- to late-summer through pollen transfer by the ground-dwelling bees and cottonseeds are formed. The resulting cottonseeds next are harvested in bulk and include a substantial concentration of seeds capable of forming $F_1$ hybrid cotton plants.

28 Claims, No Drawings

OTHER PUBLICATIONS

James B. Weaver, Jr., "Interspecific Hybrid Cotton as a Trap Crop for Boll Weevil Control", Beltwide Cotton Production Research Conference Proceedings, Las Vegas, NV, pp. 207 to 209 (1982).

Lori A. Berger, "*Agapostemon angelicus* Cockerell and Other Wild Bees as Potential Pollinators of Male-Sterile Cotton on the Texas High Plains", Master of Science Thesis, Oklahoma State University (1982).

Bernard E. Vaissiere, "Report of Progress on Hybrid Cotton Pollination Studies on the Texas High Plains", Cotton Incorporated (1982).

Frank L. Carter, Dick D. Davis and Elbert R. Jaycox, "Effect of Planting Pattern on Cross Pollination of Hybrid NX-1 Seed Production", Beltwide Cotton Production Conferences Proceedings, Atlanta, GA, pp. 130 to 131 (1984).

R. J. Kohel and C. F. Lewis, "Cotton", No. 24 in the Series Agronomy, pp. 219 to 221 (1984).

Radclyffe B. Roberts, "Bees of Northwestern America": *Agapostemon* (*Hymenoptera: Halictidae*), Technical Bulletin 125, Agric. Expt. Station, Oregon State University, Corvaillis, OR, pp. 1 to 23, Jun. 1973.

Radclyffe B. Roberts, "Bees of Northwestern America": *Halictus* (*Hymenoptera: Halictidae*), Technical Bulletin 126, Agric. Expt. Station, Oregon State University, Corvallis, OR, pp. 1 to 23, Jun. 1973.

PROCESS FOR THE ECONOMICAL PRODUCTION OF SEEDS CAPABLE OF GROWING F₁ HYBRID COTTON

BACKGROUND OF THE INVENTION

It is well known in the technical literature that when different plant lines are cross-pollinated, one can produce offspring which exhibit advantageous heterosis or hybrid vigor. Such enhanced vigor can lead to increased yields in the resulting plant product.

Cotton (i.e., plants of genus Gossypium) is recognized to be an important crop which is grown in many parts of the world. Cotton is presently being grown primarily for its lint; however, the seed may be used for planting, or a food oil may be recovered from the seeds and the residue used as a livestock feed. It also is recognized that while the necessary plants for hybrid cottonseed production are known and available, only limited hybrid cotton production has been carried out anywhere in the world to date. Such failure to practice hybrid cottonseed production on a commercial scale can be traced at least in part to the relatively high costs inherently associated with previously available cotton hybridization processes.

Representative prior publications which concern the formation of hybrid cottonseeds are the following:

(1) Canadian Pat. No. 668,452, "Production of Hybrid Cottonseed," Frank M. Eaton, Aug. 13, 1963.

(2) Vesta G. Meyer, "Male Sterility From *Gossypium harknessii*," J. of Heredity, Vol. 66, p. 23 to 27 (1975).

(3) Joseph O. Moffett, Lee S. Stith, and Charles W. Shipman, "Producing Hybrid Cotton Seed on the High Plains of Texas," Beltwide Cotton Production Research Conferences Proceedings, Atlanta, Ga., p. 90 to 92 (1977).

(4) J. B. Weaver, Jr., "Present Status of Fertility Restoration in Cytoplasmic Male-Sterile Upland Cotton," Beltwide Cotton Production Research Conferences Proceedings, Atlanta, Ga., p. 95 to 96 (1977).

(5) Joseph O. Moffett, Lee S. Stith, and Charles W. Shipman, "Producing Hybrid Cotton Seed on a Field Scale by Using Honey Bees as Pollinators," Beltwide Cotton Production Research Conferences Proceedings, Dallas, Tex., p. 77 to 79 (1978).

(6) W. R. Meredith, Jr., Vesta Meyer, B. W. Hanny, and J. C. Bailey, "Influence of Five Gossypium Species Cytoplasms on Yield, Yield Components, Fiber Properties, and Insect Resistance in Upland Cotton," Crop Science, Vol. 19, p. 647 to 650, September–October 1979.

(7) Richard H. Sheetz and James B. Weaver, Jr., "Pima Fertility Enhancer Factor: Inheritance and Use in Hybrid Cotton Production," Beltwide Cotton Production Research Conferences Proceedings, St. Louis, Mo., p. 82 (1980).

(8) R. H. Sheetz and J. B. Weaver, Jr. "Inheritance of a Fertility Enhancer Factor From Pima Cotton When Transferred Into Upland Cotton With *Gossypium harknessii* Brandegee Cytoplasm," Crop Science, Vol. 20, p. 272 to 275, March–April 1980.

(9) Joseph O. Moffett, Henry B. Cobb and Don R. Rummel, "Bees of Potential Value as Pollinators in the Production of Hybrid Cottonseed on the High Plains of Texas", Beltwide Cotton Production Research Conferences Proceedings, Bee Report No. 2, p. 1 to 12 (1980).

(10) Delbert C. Hess, "Hybrid Cotton Development," Beltwide Cotton Mechanization-Production Research Conferences Proceedings, New Orleans, La, p. 28 to 29 (1981).

(11) J. E. Quisenberry and R. E. Dilbeck, "Stormproof Boll in Upland Cotton III. Genotype-Environment Interaction and Genetic Analysis," Crop Science, Vol. 21, p. 511 to 514, July–August 1981.

(12) James B. Weaver, Jr., "Recent Significant Observations on the Development of Hybrid Cotton," Beltwide Cotton Production Research Conferences Proceedings, Las Vegas, Nev., p. 88 to 90 (1982).

(13) James B. Weaver, Jr., "Interspecific Hybrid Cotton as a Trap Crop for Boll Weevil Control," Beltwide Cotton Production Research Conferences Proceedings, Las Vegas, Nev., p. 207 to 209 (1982).

(14) Lori A. Berger, "*Agapostemon angelicus* Cockerell and Other Wild Bees as Potential Pollinators of Male-Sterile Cotton on the Texas High Plains", Master of Science Thesis, Oklahoma State University (1982).

(15) Bernard E. Vaissiere, "Report of Progress on Hybrid Cotton Pollination Studies on the Texas High Plains", Cotton Incorporated (1982).

(16) Frank L. Carter, Dick D. Davis and Elbert R. Jaycox, "Effect of Planting Pattern on Cross Pollination of Hybrid NX-1 Seed Production," Beltwide Cotton Production Conferences Proceedings, Atlanta, Ga., p. 130 to 131 (1984).

(17) R. J. Kohel and C. F. Lewis, "Cotton", No. 24 in the Series AGRONOMY, p. 219 to 221 (1984).

(18) U.S. Pat. No. 4,570,380, "Route to Hybrid Cotton Production", Levon L. Ray and Jose L. Longoria, Feb. 18, 1986.

Representative articles which discuss wild bees commonly found in the United States include:

(19) Radclyffe B. Roberts, "Bees of Northwestern America: Agapostemon (Hymenoptera: Halictidae), Technical Bulletin 125, Agric. Expt. Station, Oregon State University, Corvallis, Oreg., p. 1 to 23, June 1973.

(20) Radclyffe B. Roberts, "Bees of Northwestern America: Halictus (Hymenoptera: Halictidae), Technical Bulletin 126, Agric. Expt. Station, Oregon State University, Corvallis, OR, p. 1 to 23, June 1973.

None of the above publications teaches that hybrid cottonseeds could be reliably produced under any circumstances on a commercially feasible basis while relying upon wild bees of any type to accomplish pollen transfer.

It is an object of the present invention to provide an improved overall process for production of seeds capable of growing F₁ hybrid cotton plants.

It is an object of the present invention to provide an improved process for the production of seeds capable of growing F₁ hybrid cotton plants which makes possible excellent production cost control.

It is an object of the present invention to provide an improved process for the production of seeds capable of growing F₁ hybrid cotton plants which can be carried out on an economically advantageous basis.

It is an object of the present invention to provide an improved process for the production of seeds capable of growing F₁ hybrid cotton plants which employs primarily ground-dwelling wild bees to carry out cross-pollination on a reliable basis.

These and other objects, as well as the scope, nature, and utilization of the claimed process, will be apparent to those skilled in the art from the following detailed description and appended claims.

SUMMARY OF THE INVENTION

It has been found that an improved process for the low cost production of seeds capable of growing $F_1$ hybrid cotton plants comprises:

(a) selecting a planting area which normally possesses the appropriate climatic conditions for the growing of cotton plants and is suitable for habitation by ground-dwelling wild bees which exhibit a propensity to visit the blossoms of cotton plants, (b) growing a crop on the planting area for at least one growing season in the substantial absence of the application of an insecticide so as to encourage the habitation of the planting area by the ground-dwelling wild bees in significant numbers, (c) growing during an immediately following growing season in at least one selected portion of the planting area a block of early-blossoming plants which provide a source of pollen and nectar for the ground-dwelling wild bees during the spring and early summer sufficient for their support, (d) growing in another selected portion of the planting area during the immediately following growing season a substantially random population of (i) cytoplasmically male sterile cotton plants, and (ii) male fertile cotton plants which are capable of restoring male fertility to the progeny of the cytoplasmically male sterile cotton plants wherein the ratio of the cytoplasmically male sterile cotton plants to the male fertile cotton plants is no more than approximately 5:1, (e) refraining from applying an insecticide to the cotton plants of the planting area at least until after seed set has occurred on the cotton plants, (f) pollinating the substantially random population of cotton plants (i) and (ii) when the plants blossom during mid- to late-summer through pollen transfer by the ground-dwelling wild bees to produce cottonseeds on the cytoplasmically male sterile plants which are capable of forming male fertile $F_1$ hybrid cotton plants and cottonseeds are formed on the male fertile cotton plants (ii) via self-pollination, and (g) recovering cottonseeds formed on the substantially random population of cotton plants (i) and (ii) which include a substantial concentration of seeds capable of forming $F_1$ hybrid cotton plants when planted.

DESCRIPTION OF PREFERRED EMBODIMENTS

The improved process of the present invention makes use of the basic cytoplasmic-genetic system for hybrid cotton production reported in the literature by researchers such as Vesta G. Meyer and James B. Weaver, Jr. As described in detail hereafter, the improved process of the present invention may be carried out on a highly economical and reliable basis.

It is essential when carrying out the improved process of the present invention that one select a planting area which (1) possesses the appropriate climatic conditions for the growing of cotton, and (2) is suitable for habitation by ground-dwelling wild bees which exhibit a propensity to visit the blossoms of cotton plants. The planting area should have soil of a type which is friable and stable. Accordingly, the ground-dwelling wild bees may readily burrow for extensive distances (e.g., up to four feet or more) as is their custom without significant loss of the burrow configuration caused by tunnel collapse, etc. Preferred soils for the planting area are of the loam type (e.g., clay-loam soils, silty-loam soils, sandy-loam soils, etc.). The particularly preferred soil for the planting area is of the silty-loam type. Soils that contain too much sand generally should be avoided since they do not possess the requisite stability to maintain the walls of the burrows on a reliable basis and accordingly will not attract and retain adequate populations of ground-dwelling wild bees.

Representative counties of Texas where one may practice the improved process of the invention are Gray, Wheeler, Deaf Smith, Randall, Armstrong, Donley, Collingsworth, Parmer, Castro, Swisher, Briscoe, Hall, Childress, Bailey, Lamb, Hale, Floyd, Motley, Cottle, Foard, Hardeman, Willbarger, Wichita, Cochran, Hockley, Lubbock, Crosby, Dickens, King, Knox, Baylor, Archer, Clay, Montague, Cook, Grayson, Fannin, Lamar, Red River, Bowie, Yoakum, Terry, Lynn, Garza, Kent, Stonewall, Haskel, Throckmorton, Young, Wise, Denton, Collin, Hunt, Delta, Gaines, Dawson, Borden, Scurry, Fisher, Jones, Shackelford, Palo Pinto, Tarrant, Dallas, Rockwell, Kaufman, Van Zandt, Andrews, Martin, Howard, Mitchell, Nolan, Taylor, Johnson, Ellis, El Paso, Hudspeth, Reeves, Presido, Pecos, Midland, Glasscock, Upton, Reagan, Tom Green, Schleicher, Runnels, Coleman, Hamilton, Bosque, Coryell, Somerwell, Hill, Navarro, McLennan, Limestone, Bell, Falls, Milam, Robertson, Leon, Houston, Williamson, Travis, Burieson, Brazos, and Zavala.

Representative counties of Oklahoma where one may practice the improved process of the present invention are Roger Wills, Beckham, Greer, Harmon, Jackson, Dewey, Custer, Washita, Kiowa, Tillman, Blaine, Caddo, Comanche, Cotton, Canadian, Grady, Stephens, Jefferson, Logan, McClain, Garvin, Bryan, Muskogee, and McCurtain.

Representative counties of New Mexico where one may practice the improved process of the present invention are Roosevelt, Chaves, Eddy, Lea, Luna, and Don Anna.

Representative counties in Arkansas where one may practice the improved process of the present invention are Johnson, Yell, Conway, Pulaski, Lonoke, Jefferson, Prairie, Arkansas, Lincoln, Desha, Drew, Ashley, Chicot, Jackson, Woodruf, Monroe, Clay, Green, Craighead, Poinsett, Cross, St. Francis, Lee, Phillips, Mississippi, and Crittenden.

Representative counties of Missouri where one may practice the improved process of the present invention are Butler, Stoddard, Scott, Mississippi, New Madrid, and Penscott.

Representative counties in Tennessee where one may practice the improved process of the present invention are Obion, Weakley, Henry, Dyer, Gibson, Carroll, Lauderdale, Haywood, Madison, Tipton, Shelly, Fayette, Hardeman, McNairy, Hardin, Giles, Lake, Chester, Henderson, and Decatur.

Representative counties of Alabama where one may practice the improved process of the present invention are Lauderdale, Colbert, Franklin, Lawrence, Limestone, Madison, Morgan, Jackson, Marshall, DeKalb, Cullman, Blount, Etowah, Cherokee, Calhoun, Taladega, Shelby, Chilton, Bibb, Tuscalosa, Pickens, Lamar, Fayette, Marion, Sumpter, Greene, Hale, Marengo, Perry, Chocktaw, Washington, Clark, Wilcox, Monroe, Baldwin, Escambia, Conecuh, Butler, Covington, Geneva, Houston, Coffee, Barbour, Russell, Lee, Macon, Montgomery, Elmore, Autauga, Lowndes, Dallas, and Tallapoosa.

Representative counties of Georgia where one may practice the improved process of the present invention are Johnson, Laurens, Twiggs, Dodge, Crawford, Taylor, Peach, Houston, Macon, Dooly, Pulaski, Wilcox, Crisp, Sumpter, Lee, Worth, Turner, Tift, Irwin, Ben Hill, Coffee, Cook, Colquitt, Thomas, Brooks, Mitchell, Miller, Seminole, Early, Clay, Calhoun, Randolph, Terrell, Stewart, Bleckley, Hart, Elbert, Madison, Oconee, Walton, Morgan, Newton, Henry, Covetta, Meriwether, Chattooga, Gordon, Floyd, Polk, Bartow, Richmond, Burke, Screven, Jenkins, Manuel, Chandler, Treutlen, McDuffin, Warren, Glascock, Jefferson, and Washington.

Representative counties of South Carolina where one may practice the improved process of the present invention are Greenville, Spartanburg, Cherokee, York, Chester, Anderson, Laurens, Abbeville, Greenwood, Saluda, Edgefield, Aiken, Barnwell, Allendale, Hampton, Bamberg, Lexington, Richland, Kershaw, Chesterfield, Marlboro, Darlington, Dillon, Marion, Florence, Sumter, Williamsburg, Clarendon, Lee, Calhoun, and Orangeburg.

Representative counties of North Carolina where one may practice the improved process of the present invention are North Hampton, Hartford, Halifax, Nash, Edgecombie, Harnett, Cumberland, Samson, Hoke, Roberson, Scotland, Richmond, Anson, Union, Rutherford, and Cleveland.

A representative county in Virginia where one may practice the improved process of the present invention is Greensville.

Representative counties of Florida where one may practice the improved process of the present invention are Escambia, Santa Rosa, Holmes, Walton, and Okaloosa.

Representative counties of Tennessee where one may practice the improved process of the present invention are Lincoln, Bedford, and Franklin.

The improved process of the present invention similarly may be carried out in other cotton-growing areas of the world which are suitable for habitation by ground-dwelling wild bees.

Representative ground-dwelling wild bees for use in the process of the present invention are of the family Halictidae, or of the genus Bombus. Representative members of the Family Halictidae are *Agapostemon angelicus, Halictus ligatus, Melissodes thelypodii, Svastra atryses*, members of the genus Dialictus (formerly known as Evylaeus), combinations of two or more of these, etc. The particularly preferred member of the Family Halictidae is *Agapostemon angelicus*. Representative members of the genus Bombus are *Bombus fraternus, Bombus americanorum, Bombus borealis, Bombus fervidus, Bombus huntii, Bombus nevadensis*, etc. The particularly preferred member of the genus Bombus is *Bombus fraternus*. The ground-dwelling wild bees employed when carrying out the process of the present invention tend to spend nights living in burrows in the ground. They tend to live a solitary existence during most of their life cycles and the female bees often tend to spend the winter as pregnant females while present in the ground in deep burrows. For a discussion of bee lifecycles and the ability of bees to overwinter, see "An Introduction to the Study of Insects", Fourth Edition, by Donald J. Borroc, Dwight M. DeLong and Charles A. Tripelhorn of Ohio State University (Holt, Rhinehart and Winston). See particularly the helpful chart found at p. 72 of that treatise.

The population of ground-dwelling wild bees is encouraged at the planting area through the substantial absence for at least one growing season (e.g., 1 to 3 or more growing seasons) of the application of an insecticide which could harm or otherwise repel such bees. During the at least one preceding or antecedent growing season a crop other than cotton commonly is grown which forms sufficient pollen and nectar to well support the ground-dwelling wild bees and which also will be beneficial to the farmer. Representative crops which may be grown during the at least one preceding growing season are corn, sorghum, soybeans, pasture grasses, pearl millet, German millet, canola, sunflowers, wild flowers (especially those of the Compositae family such as daisies), etc., and combinations of two or more of these. Corn and sorghum are particularly preferred since they return relatively large amounts of organic material to the soil and render the soil particularly well suited for burrowing by the ground-dwelling wild bees. They also provide copious amounts of pollen. Alternatively, cotton may be grown in the planting area during the preceding growing season provided no insecticide is utilized which would interfere with the ground-dwelling wild bee population. At the conclusion of the at least one preceding growing season the planting area is inhabited by significant numbers of the ground-dwelling wild bees, and such habitation will make possible the presence of large numbers of the requisite pollinators in the planting area during the immediately following growing season which are sufficient to accomplish the desired cross-pollination.

During the immediately following growing season at least one selected portion of the planting area is used to grow a block of early-blossoming plants which provide a source of pollen and nectar for the ground-dwelling wild bees during the spring and early summer sufficient for their support. Approximately 5 to 10 percent of the planting area commonly is planted with such early-blossoming plants. In some instances it may be desirable that larger or smaller portions of the planting area bear the early-blossoming plants. The proportion of the planting area which is planted with the early-blossoming plants will be influenced by their relative propensity to form pollen and nectar under the growing conditions encountered. A plurality of blocks of such early-blossoming plants may be present in the planting area and take the configuration of spaced parallel strips which traverse the planting area. Alternatively, the early-blossoming plants may be planted as a border which surrounds all or a portion of the planting area or otherwise be dispersed as a plurality of blocks which are scattered throughout the planting area in a pattern whereby cotton plants will always be nearby (e.g., immediately adjacent).

Representative early-blossoming plants for use in the process of the present invention are Leguminosae, Compositae, and Brassicaceae.

Representative plants of the Leguminosae family for use in the present process include alfalfa, clovers, vetch, sweet peas, common beans, locust trees, etc. Representative plants of the Compositae family for use in the present process include sunflowers, daisies, marigolds, dandelions, etc. Representative plants of the Brassicaceae family for use in the present process include the *Brassica napus* and *Brassica campestris* forms of canola, plus wild forms of Brassica such as penney cress, yellow mustard, etc. Commonly, the early-blossoming plants selected for growing in the planting area will inherently tend to blossom early in the growing season and will inherently produce a diminished supply of pollen and nectar at the time of the cotton pollination (discussed hereafter). However, at the time of cotton pollination the blossoming of such plants optionally may be terminated or diminished by the intervention of man such as by cutting, disking, or harvesting for hay, seed, etc.

During the same immediately following growing season a substantially random population of (i) cytoplasmically male sterile cotton plants, and (ii) male fertile cotton plants which are capable of restoring male fertility to the progeny of the male sterile cotton plants are grown in at least one other selected portion of the planting area. The ratio of cytoplasmically male sterile cotton plants to the male fertile cotton plants is no more than approximately 5:1 (e.g., 3:1 to 5:1). In a preferred embodiment the ratio of cytoplasmically male sterile cotton plants to the male fertile cotton plants is no more than approximately 4:1. Particularly good results have been achieved when the ratio of cytoplasmically male sterile cotton plants to male fertile cotton plants is approximately 4:1. Lower ratios may be used but these tend to interfere with the advantageous economics of the hybrid cottonseed production made possible by the present invention. The substantially random population of cotton plants preferably is grown in rows. Such rows commonly have a spacing of approximately 30 to 40 inches between rows, and a spacing of approximately 2 to 12 inches between cotton plants within rows. Such random population of cotton plants is grown nearby the early-blossoming plants previously discussed and commonly on substantially all of the remaining portion of the planting area. Accordingly, when the cotton plants blossom during mid- to late-summer, the ground-dwelling wild bees which inhabit the planting area can readily perceive such cotton blossoms and visit them in search of pollen and nectar. Such blossoming of the cotton plants commonly takes place during July and August in the northern hemisphere.

In a preferred embodiment of the process of the present invention fertility restoring cotton plants are selected for growing in the planting area which commence blossoming prior to the cytoplasmically male sterile cotton plants and which blossom substantially throughout the time the cytoplasmically male sterile cotton plants are receptive to receive pollen. This helps to insure an adequate supply of pollen at the appropriate time to accomplish a high level of cross-pollination.

Additionally, it is preferred that the cytoplasmically male sterile cotton plants and the male fertility restoring cotton plants each possess a different genetic marker which can be used to visually distinguish their respective progeny. A distinctive pollen coloration in the progeny plants is an example of such a marker. For instance, the cytoplasmically male sterile cotton plants preferably may possess homozygous dominant genes for yellow pollen coloration and the fertility-restoring cotton plants may possess homozygous recessive genes for cream pollen coloration. Other representative genetic markers which can be used to distinguish the progeny plants include nectarless vs. nectared plants, flower color in *Gossypium hirsutum* × *Gossypium barbendense*, okra leaf cytoplasmically male sterile plants × normal leaf restorer plants, etc. Such markers can be introduced into pre-existing lines of the parent cotton plants while using conventional plant breeding techniques.

In a further preferred embodiment of the process of the present invention, the cottonseeds formed on the cytoplasmically male sterile cotton plants and on the fertility-restoring cotton plants each possess a different genetically-derived visual appearance which can be used as a basis for their substantial separation. Suitable bases for such separation include overall seed size, seed length, other distinctive morphological shapes, etc. In a particularly preferred embodiment a seed size differential is employed with the seeds formed on the cytoplasmically male sterile cotton plants being large and the seeds formed on the fertility-restoring cotton plants being small. Such genetically-derived means for differentiating the resulting seeds can be introduced into preexisting lines of the parent cotton plants while using conventional plant breeding techniques.

Suitable cytoplasmically male sterile and fertility-restoring cotton lines for use when carrying out the process of the present invention previously have been reported by researchers such as Vesta G. Meyer and James B. Weaver, Jr. and presently are available from public and private cotton breeding programs. The cytoplasmically male sterile plants commonly possess a *Gossypium harknessii* Brandegee cytoplasm and the fertility-restoring cotton plants commonly possess a *Gossypium hirsutum* cytoplasm. The cytoplasmically male sterile plants may possess the rfrfee genotype and the fertility-restoring cotton plants may possess the RfRfEE genotype. The RfRf genes commonly are derived from *Gossypium harknessii* and the EE genes commonly are derived from *Gossypium barbendense*. Appropriate test crosses which are known to those skilled in the art can be made to determine the presence of the requisite cytoplasms and genes. Fertility-restoring cotton plants are used in the process of the present invention which provide complete fertility restoration in the resulting $F_1$ hybrids. Suitable cytoplasmically male sterile cotton plants and suitable fertility-restoring cotton plants for use in the process of the present invention, as well as suitable maintainer cotton plants, are available from the Agronomy Departments of the University of Georgia (Athens, Ga.), New Mexico State University (Las Cruces, N. Mex.), Mississippi State University (Starksville, Miss.), and Texas A&M University (Lubbock, Tex.). A preferred cytoplasmically male sterile cotton line for use in the process of the present invention has been designated A5 and has been deposited in the National Cotton Collection maintained by Dr. A. E. Percival of the U.S. Department of Agriculture, Southern Crops Research Laboratory, Crop Germplasm Research Unit, College Station, Tex. 77840. A preferred maintainer line for this cytoplasmically male sterile line has been designated B5 and has been deposited in the same depository. A preferred fertility-restoring cotton line for use in the process of the present invention has been designated R1019 and has been deposited in the same depository. Samples of these seeds are available to the public and additionally will be submitted by Dr. Percival to the National Seed Storage Laboratory at Fort Collins, Colo.

It is important that no insecticide be applied to the cotton plants growing in the planting area at least until after seed set on the cotton plants has occurred. If a bollworm (Heliothus) insect problem becomes apparent in the cotton plants, an insecticide may be applied at the early boll stage in the plant's life cycle. However, if an insecticide is utilized, the planting area likely will be unsuitable for carrying out the claimed process during the next following growing season.

When the substantially random population of cytoplasmically male sterile and male fertile fertility-restoring cotton plants blossom during mid-summer to late-summer pollen transfer is made by the ground-dwelling wild bees which inhabit the planting area. As indicated such blossoming and pollination commonly take place during July and August in the northern hemisphere. Cottonseeds are formed on the cytoplasmically male sterile cotton plants which are capable of forming male fertile $F_1$ hybrid cotton plants. Cottonseeds are formed on the male fertile fertility-restoring cotton plants as a result of self-pollination.

The desired pollination may be further enhanced by taking steps to make the cotton blossoms particularly attractive to the ground-dwelling wild bees. For instance, a fertilizer such as 10-20-20, which is relatively high in potassium and phosphorus may be applied to the cotton plants at the seedling emergence stage of their development in order to encourage the abundant production of pollen and nectar. Alternative means to encourage cotton blossom visitation by the ground-dwelling wild bees include limiting irrigation at the appropriate time so that the nectar will be more concentrated in the blossoms, etc.

At the appropriate time in the life cycle of the cotton plants, the cotton is harvested and cottonseeds are recovered in bulk from the substantially random population of cotton plants growing in the planting area. Conventional harvesting technology is utilized with care being taken to avoid contamination with cottonseeds from a foreign source. No attempt is made to separately harvest the $F_1$ hybrid cottonseeds formed on the male sterile parents or the seeds formed on the male fertile restorer plants as a result of self-pollination. The resulting cottonseed product contains a substantial concentration of seeds capable of forming $F_1$ hybrid cotton plants.

A representative portion of the cottonseeds which are recovered in bulk from the planting area may be grown and the approximate proportion of $F_1$ hybrid cottonseeds therein determined on basis of a genetic marker (e.g., a distinctive pollen coloration) as previously discussed. This test planting may be carried out during the following fall and winter at a different area of the world having a mild climate such as Mexico, Chile or Puerto Rico. The remainder of the cottonseeds then may be appropriately labeled with respect to hybrid content when marketed for growing by farmers during the next planting season. In a preferred embodiment, the product contains at least 75 percent of cottonseeds by number which are capable of forming $F_1$ hybrid cotton plants. In a particularly preferred embodiment, the product contains at least 80 percent of cottonseeds by number which are capable of forming $F_1$ hybrid cotton plants.

When the two types of cottonseeds produced in the planting area are provided with different genetically-derived appearances (e.g., a seed size differential), they optionally next may be substantially separated on the basis of appearance in order to improve the purity of the $F_1$ hybrid cottonseeds. For instance, when a seed size differential exists, appropriate sieves or other seed-sorting devices may be utilized. Alternatively, when the two types of cottonseeds are of different colors, photoelectric seed sorters may be used to accomplish the desired separation. A product which contains at least 95 percent cottonseeds by number which are capable of growing $F_1$ hybrid cotton plants may be formed following removal of seeds which are the result of self-pollination. The non-hybrid product is separated and may be put to conventional uses. However, it is not essential that such seed separation be carried out since the farmer may advantageously plant the cottonseed mixture which contains a substantial concentration of seeds capable of forming $F_1$ hybrid plants.

The $F_1$ hybrid cotton plants made possible by the process of the present invention exhibit worthwhile heterosis and make possible increased cotton yields for the farmer. For instance, increased cotton yields of 5 to 20 percent have been demonstrated.

Although the invention has been described with preferred embodiments, it is to be understood that variations and modifications may be resorted to, as well be apparent to those skilled in the plant sciences. Such variations and modifications are to be considered within the purview and scope of the appended claims.

I claim:

1. An improved process for the low cost production of seeds capable of growing $F_1$ hybrid cotton plants comprising:
   (a) selecting a planting area which normally possesses the appropriate climatic conditions for the growing of cotton plants and is suitable for habitation by ground-dwelling wild bees which exhibit a propensity to visit the blossoms of cotton plants,
   (b) growing a crop on said planting area for at least one growing season in the substantial absence of the application of an insecticide so as to encourage the habitation of said planting area by said ground-dwelling wild bees in significant numbers,
   (c) growing in at least one selected portion of said planting area during an immediately following growing season a block of early-blossoming plants which provide a source of pollen and nectar for said ground-dwelling wild bees during the spring and early summer sufficient for their support,
   (d) growing in another selected portion of said planting area during said immediately following growing season a substantially random population of (i) cytoplasmically male sterile cotton plants, and (ii) male fertile cotton plants which are capable of restoring male fertility to the progeny of said cytoplasmically male sterile cotton plants wherein the ratio of said cytoplasmically male sterile cotton plants to said male fertile cotton plants is no more than approximately 5:1,
   (e) refraining from applying an insecticide to said cotton plants of said planting area at least until after seed set has occurred on said cotton plants,
   (f) pollinating said substantially random population of cotton plants (i) and (ii) when said plants blossom during mid- to late-summer through pollen transfer by said ground-dwelling wild bees to produce cottonseeds on said cytoplasmically male sterile plants which are capable of forming male fertile $F_1$ hybrid cotton plants and cottonseeds are formed on said male fertile cotton plants (ii) via self-pollination, and
   (g) recovering cottonseeds formed on said substantially random population of cotton plants (i) and (ii) which include a substantial concentration of seeds capable of forming $F_1$ hybrid cotton plants when planted.

2. An improved process for the low cost production of seeds capable of growing $F_1$ hybrid cotton plants according to claim 1 wherein the soil of said planting area is of the loam type.

3. An improved process for the low cost production of seeds capable of growing F₁ hybrid cotton plants according to claim 1 wherein said ground-dwelling wild bees are primarily of the Family Halictidae.

4. An improved process for the low cost production of seeds capable of growing F₁ hybrid cotton plants according to claim 1 wherein said ground-dwelling wild bees are primarily of the genus Bombus.

5. An improved process for the low cost production of seeds capable of growing F₁ hybrid cotton plants according to claim 1 wherein said ground-dwelling wild bees are selected from the group consisting of *Agapostemon angelicus, Halictus ligatus, Melissodes thelypodii, Svastra atryses,* genus Dialictus, *Bombus fraternus, Bombus americanorum, Bombus borealis, Bombus fervidus, Bombus huntii, Bombus nevadensis,* and combinations of two or more of the foregoing.

6. An improved process for the low cost production of seeds capable of growing F₁ hybrid cotton plants according to claim 1 wherein said ground-dwelling wild bees are primarily *Agapostemon angelicus.*

7. An improved process for the low cost production of seeds capable of growing F₁ hybrid cotton plants according to claim 1 wherein said crop which is grown in step (b) is selected from the group consisting of corn, soybeans, sorghum, pasture grasses, pearl millet, German millet, canola, sunflowers, wild flowers, and combinations of two or more of the foregoing.

8. An improved process for the low cost production of seeds capable of growing F₁ hybrid cotton plants according to claim 1 wherein said early-blossoming plants of step (c) are selected from the group consisting of Leguminosae, Compositae, and Brassicaceae.

9. An improved process for the low cost production of seeds capable of growing F₁ hybrid cotton plants according to claim 1 wherein said early-blossoming plants of step (c) are alfalfa.

10. An improved process for the low cost production of seeds capable of growing F₁ hybrid cotton plants according to claim 1 wherein said block of early-blossoming plants of step (c) produce a diminished supply of pollen and nectar at the time of said cotton pollination of step (f).

11. An improved process for the low cost production of seeds capable of growing F₁ hybrid cotton plants according to claim 1 wherein said substantially random population of cotton plants (i) and (ii) of step (d) is planted in rows.

12. An improved process for the low cost production of seeds capable of growing F₁ hybrid cotton plants according to claim 1 wherein said male fertile cotton plants (ii) of step (d) commence blossoming prior to said cytoplasmically male sterile cotton plants (i) and blossom substantially throughout the time period when said cytoplasmically male sterile cotton plants (i) are receptive to receive pollen.

13. An improved process for the low cost production of seeds capable of growing F₁ hybrid cotton plants according to claim 1 wherein said pollination of step (f) takes place during July and August.

14. An improved process for the low cost production of seeds capable of growing F₁ hybrid cotton plants according to claim 1 wherein said cotton plants (i) and (ii) each possess a genetic marker which can be used to visually distinguish their respective progeny.

15. An improved process for the low cost production of seeds capable of growing F₁ hybrid cotton plants according to claim 14 wherein said marker is pollen coloration.

16. An improved process for the low cost production of seeds capable of growing F₁ hybrid cotton plants according to claim 15 wherein said cytoplasmically male sterile cotton plants (i) possess homozygous dominant genes for yellow pollen coloration and said male fertile cotton plants (ii) possess homozygous recessive genes for cream pollen coloration.

17. An improved process for the low cost production of seeds capable of growing F₁ hybrid cotton plants according to claim 1 wherein during step (d) the ratio of said cytoplasmically male sterile cotton plants to said male fertile cotton plants is no more than 4:1.

18. An improved process for the low cost production of seeds capable of growing F₁ hybrid cotton plants according to claim 1 wherein during step (d) the ratio of said male sterile cotton plants to said male fertile cotton plants is approximately 4:1.

19. An improved process for the low cost production of seeds capable of growing F₁ hybrid cotton plants according to claim 1 wherein said substantially random population of step (d) is grown in rows having a spacing of approximately 30 to 40 inches between rows, and a spacing of approximately 2 to 12 inches between plants within said rows.

20. An improved process for the low cost production of seeds capable of growing F₁ hybrid cotton plants according to claim 1 wherein at least 75 percent of the cottonseeds recovered in step (g) are capable of growing F₁ hybrid cotton plants.

21. An improved process for the low cost production of seeds capable of growing F₁ hybrid cotton plants according to claim 1 wherein at least 80 percent of the cottonseeds recovered in step (g) are capable of growing F₁ hybrid cotton plants.

22. An improved process for the production of seeds capable of growing F₁ hybrid cotton plants according to claim 14 which includes the additional steps of (h) growing at least a portion of the cottonseeds recovered in step (g) and (i) determining the approximate proportion of F₁ hybrid cottonseeds present in said cottonseeds recovered in step (g) on the basis of said genetic marker.

23. An improved process for the production of seeds capable of growing F₁ hybrid cotton plants according to claim 15 which includes the additional steps of (h) growing at least a portion of the cottonseeds recovered in step (g) and (i) determining the approximate proportion of F₁ hybrid cottonseeds present in said cottonseeds recovered in step (g) on the basis of said pollen coloration.

24. An improved process for the production of seeds capable of growing F₁ hybrid cotton plants according to claim 16 which includes the additional steps of (h) growing at least a portion of the cottonseeds recovered in step (g) and (i) determining the approximate proportion of F₁ hybrid cottonseeds present in said cottonseeds of step (g) on the basis of the yellow pollen coloration exhibited by plants formed by said seeds capable of growing F₁ hybrid cotton plants.

25. An improved process for the production of seeds capable of growing F₁ hybrid cotton plants according to claim 1 wherein cottonseeds formed on said substantially random population of cotton plants (i) and (ii) are capable of being substantially separated following step (g) on the basis of a genetically-derived visual appearance.

26. An improved process for the production of seeds capable of growing $F_1$ hybrid cotton plants according to claim 25 wherein said genetically-derived visual appearance is a disparity in seed size.

27. An improved process for the production of seeds capable of growing $F_1$ hybrid cotton plants according to claim 25 which includes the additional step (h) of substantially separating said seeds on the basis of said genetically-derived visual appearance.

28. An improved process for the production of seeds capable of growing $F_1$ hybrid cotton plants according to claim 26 which includes the additional step (h) of substantially separating said seeds on the basis of said disparity in seed size.

* * * * *